US009504662B2

(12) United States Patent
Park et al.

(10) Patent No.: US 9,504,662 B2
(45) Date of Patent: Nov. 29, 2016

(54) COMPOSITION FOR SKIN IMPROVEMENT COMPRISING HEXAMIDINES AND RETINOIDS

(75) Inventors: Jong Hee Park, Yongin-si (KR); Shin Young Park, Seoul (KR); Hong-Ju Shin, Seongnam-si (KR); Do-Hoon Kim, Yongin-si (KR); Chang-Geun Yi, Yongin-si (KR); Won Seok Park, Seoul (KR); Hyun Ju Koh, Anyang-si (KR); Jeong-Hwan Kim, Paju-si (KR); Hyoung Jun Kim, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 551 days.

(21) Appl. No.: 13/390,476

(22) PCT Filed: Aug. 20, 2010

(86) PCT No.: PCT/KR2010/005541
§ 371 (c)(1),
(2), (4) Date: Feb. 14, 2012

(87) PCT Pub. No.: WO2011/021892
PCT Pub. Date: Feb. 24, 2011

(65) Prior Publication Data
US 2012/0149773 A1    Jun. 14, 2012

(30) Foreign Application Priority Data
Aug. 20, 2009    (KR) .................. 10-2009-0077158

(51) Int. Cl.
| A61K 31/155 | (2006.01) |
| A61K 31/16 | (2006.01) |
| A61K 31/07 | (2006.01) |
| A61K 31/203 | (2006.01) |

(52) U.S. Cl.
CPC ........... *A61K 31/155* (2013.01); *A61K 31/203* (2013.01)

(58) Field of Classification Search
USPC .................. 514/552, 625, 631, 636, 763, 72
See application file for complete search history.

(56) References Cited

U.S. PATENT DOCUMENTS

| 4,505,924 | A | 3/1985 | Taylor et al. |
| 5,607,980 | A * | 3/1997 | McAtee et al. ............... 514/476 |
| 5,679,374 | A | 10/1997 | Fanchon et al. |
| 2002/0143059 | A1* | 10/2002 | Pillai et al. .................. 514/557 |
| 2004/0120918 | A1 | 6/2004 | Lintner et al. |
| 2004/0176273 | A1* | 9/2004 | Bissett .............................. 514/2 |
| 2006/0263400 | A1 | 11/2006 | Bissett |
| 2006/0269504 | A1 | 11/2006 | James |
| 2010/0286102 | A1* | 11/2010 | Vielhaber ................ A61K 8/34 514/171 |

FOREIGN PATENT DOCUMENTS

| CN | 1482899 A | 3/2004 |
| CN | 1662216 A | 8/2005 |
| KR | 10-2006-0014047 | 2/2006 |
| KR | 10-2007-0056170 | 5/2007 |
| KR | 10-2008-0000605 A | 1/2008 |
| KR | 10-0864746 B1 | 10/2008 |
| WO | WO 02/02074 A2 | 1/2002 |
| WO | WO 2004/078158 A2 | 9/2004 |
| WO | WO 2005/011627 A2 | 2/2005 |

OTHER PUBLICATIONS

Office Action from Chinese Application No. 201080047407.X mailed Dec. 4, 2012.
Office Action from Chinese Application No. 201080047407.X mailed Aug. 16, 2013.
International Search Report for corresponding International Application No. PCT/KR2010/005541 (Form PCT/ISA/210).
Office Action from Korean Patent Application No. 10-2009-0077158 (mailed Mar. 14, 2014).
Notice of Allowance from Korean Patent Application No. 10-2009-0077158 (mailed Sep. 12, 2014).
Office Action for Chinese Patent Application No. 201410161736.7 (issued Jul. 21, 2015).
Office Action for Chinese Patent Application No. 201410161736.7 (issued Mar. 17, 2016).
Wei Jing et al., "Function of Ceramides in Skin and Application in Cosmetic", Cereals & Oils, 2007, vol. 1, pp. 21-24.
Ling guan ting, "Handbook of Health Food Ingredients", Chemical Industry Press, First Edition, 2003, pp. 609-610.

* cited by examiner

*Primary Examiner* — Shobha Kantamneni
(74) *Attorney, Agent, or Firm* — Merchant & Gould P.C.

(57) ABSTRACT

Disclosed is herein a composition comprising hexamidines, derivatives thereof, or pharmaceutically acceptable salts thereof; and retinoids, derivatives thereof, or pharmaceutically acceptable salts thereof, as an active ingredient. The composition of the present invention has effects for preventing, improving or treating acne; controlling sebum; pore-controlling; and preventing, improving or treating skin pigmentation. Also, the composition of the present invention could alleviate skin-irritations caused with retinoids by including ceramides.

5 Claims, 5 Drawing Sheets

COMPOSITION FOR SKIN IMPROVEMENT COMPRISING HEXAMIDINES AND RETINOIDS

This application is a U.S. National Stage Application under 35 U.S.C. §371 of International Patent Application No. PCT/KR2010/005541, filed 20 Aug. 2010, which claims the benefit of priority to Korean Patent Application No. 10-2009-0077158, filed 20 Aug. 2009, the disclosures of all of which are hereby incorporated by reference in their entireties. The International Application was published in Korean on 24 Feb. 2011 as WO 2011/021892. To the extent appropriate, a claim of priority is made to each of the above disclosed applications.

TECHNICAL FIELD

This disclosure relates to a composition for improving skin conditions, which containing hexamidine or a derivative or pharmaceutically acceptable salt thereof in combination with retinoid or a derivative or pharmaceutically acceptable salt thereof.

BACKGROUND

Acne is an inflammatory disease occurring in hair follicles in skin and sebaceous glands. Internal causes of acne include secretion of sebum and disorders in ingredients of sebum, caused by endocrine actions such as a change in hormones including cortisol secreted by stress or progesterone related to menstruation, and imperforation in sebaceous glands and hair follicles caused by hypersecretion of sebum.

External causes of acne include an increase in sebum, which causes stimulation factors of *Propionibacterium acnes* living in sebaceous glands to stimulate the epithelial walls of hair follicles so that the corneous layers of inner surfaces of the epithelium are thickened, resulting in imperforation caused by abnormal keratinization of hair follicles and a decrease in oxygen introduction into hair follicles. Such conditions are favorable to the growth of anaerobic *P. acnes*, the cause of acne, and thus accelerate the growth of *P. acnes* in lesions of acne.

Meanwhile, approximately 0.05-0.4 mg/cm$^2$ of sebum always exists on the skin surface. Such sebum is produced through two different paths: sebaceous lipids such as triglycerides, squalane or wax esters, and epidermal lipids produced between epithelial cells, such as phospholipids or, cholesterols.

Sebum is combined with water, such as sweat, to form a thin sebum layer in the form of weak acidic emulsion on the skin surface, so that it functions as a luburicant on the skin surface, prevents introduction of external foreign materials and evaporation of water in the skin, and protects skin from various types of physical and chemical irritations.

However, it is reported that excessive sebum causes seborrheic dermatitis, such as acne, and lipid peroxides produced by UV rays are one of the causes of skin irritation.

SUMMARY OF THE INVENTION

Technical Problem

It has now been found that use of hexamidine or a derivative or pharmaceutically acceptable salt thereof in combination with retinoid or a derivative or pharmaceutically acceptable salt thereof provides a synergic effect to accomplish significantly good effects of preventing, improving and treating acne, controlling sebum, controlling pores, and preventing, improving and treating skin pigmentation. Therefore, this disclosure is directed to providing a composition for improving skin conditions, which contains hexamidine or a derivative or pharmaceutically acceptable salt thereof in combination with retinoid or a derivative or pharmaceutically acceptable salt thereof, as active ingredients.

Technical Solution

In one general aspect, there is provided a composition for preventing, improving or treating acne, including hexamidine or a derivative or pharmaceutically acceptable salt thereof in combination with retinoid or a derivative or pharmaceutically acceptable salt thereof, as active ingredients.

In another general aspect, there is provided a composition for controlling sebum, including hexamidine or a derivative or pharmaceutically acceptable salt thereof in combination with retinoid or a derivative or pharmaceutically acceptable salt thereof, as active ingredients.

In still another general aspect, there is provided a composition for controlling pores, including hexamidine or a derivative or pharmaceutically acceptable salt thereof in combination with retinoid or a derivative or pharmaceutically acceptable salt thereof, as active ingredients.

In yet another general aspect, there is provided a composition for preventing, improving or treating skin pigmentation, including hexamidine or a derivative or pharmaceutically acceptable salt thereof in combination with retinoid or a derivative or pharmaceutically acceptable salt thereof, as active ingredients.

Advantageous Effects

The composition disclosed herein comprises hexamidine or a derivative or pharmaceutically acceptable salt thereof in combination with retinoid or a derivative or pharmaceutically acceptable salt thereof, as active ingredients, and thus provides, through the synergic effect of the ingredients, excellent effects of preventing, improving and treating acne, controlling sebum, controlling pores, and preventing, improving and treating skin pigmentation.

When the composition including hexamidine or a derivative or pharmaceutically acceptable salt thereof in combination with retinoid or a derivative or pharmaceutically acceptable salt thereof, as active ingredients, further comprises a ceramide, it provides an effect of alleviating skin irritation.

BRIEF DESCRIPTION OF THE DRAWINGS

FIG. 2 shows UV photographs showing the results of Test Example 2 in which sebum distribution is determined before the test and 4 weeks after the test using no treatment, and using application of hexamidine, retinol, or hexamidine and retinol on the face (Portions a and b are the photographs before the test and 4 weeks after the test using no treatment; Portions c and d are the photographs before the test and 4 weeks after the test using application of Comparative Example 1; Portions e and f are the photographs before the test and 4 weeks, after the test using application of Comparative Example 2; and Portions g and h are the photographs before the test and 4 weeks after the test using application of Example 1, wherein sebum is shown in the form of light dots (red dots represent oxidized sebum, while green and yellow dots represent non-oxidized sebum));

DETAILED DESCRIPTION

In one aspect, there is provided a composition for preventing, improving and treating acne, controlling sebum, controlling pores, and preventing, improving and treating skin pigmentation, the composition including hexamidine or a derivative or pharmaceutically acceptable salt thereof in combination with retinoid or a derivative or pharmaceutically acceptable salt thereof, as active ingredients.

According to an embodiment, the composition comprises hexamidine or a derivative or pharmaceutically acceptable salt thereof. As used herein, hexamidine or a derivative or pharmaceutically acceptable salt thereof also includes an isomer thereof. According to a particular embodiment, hexamidine or a derivative or pharmaceutically acceptable salt thereof may include hexamidine, hexamidine isethionate or hexamidine diisethionate.

The effect of destroying *Propionibacterium acnes* of hexamidine or a derivative or pharmaceutically acceptable salt thereof is better than the effect of a conventional disinfectant, 70% alcohol. Therefore, when applying the composition according to an embodiment to skin, it is possible to destroy *P. acne*, the cause of acne. Thus, it is expected that the composition provides an effect of preventing, improving or treating acne.

The composition according to an embodiment comprises retinoid or a derivative or pharmaceutically acceptable salt thereof. As used herein, retinoids are a class of chemical compounds related chemically to vitamin A, and include vitamin A, as well as any natural and/or synthetic analogues thereof, compounds having the biological activities of vitamin A on skin, and isomers thereof. Particularly, retinoids include retinol, retinal, retinoic acid and derivatives thereof. According to an embodiment, retinoids may include retinol, and retinyl esters, including retinyl palmitate, retinyl acetate and retinyl propionate.

Retinoids accelerate cell differentiation, help collagen synthesis to increase skin elasticity, stimulate metabolism in skin corneous layers to inhibit hyperkeratinization of pores and to make skin smooth, prevent skin boils and pimples, and control sebaceous glands to inhibit hypersecretion of sebum. For example, 4 μM of retinol substantially has the same degree of sebum-inhibiting effect as 100 nM of Isotretinoin used as a prescription only medicine for treating acne. However, it is reported that Isotretinoin may cause malformed children when pregnant women use it and become a cause of depression, and thus it should be treated with extra caution. On the contrary, retinoids have no such side effects. Therefore, when applying the composition according to an embodiment to skin, it is possible to provide an effect of controlling and inhibiting skin sebum without the above-mentioned side effects, thereby reducing acne generation caused by hypersecretion of sebum and improving skin conditions.

In addition, the composition according to an embodiment inhibits hyperkeratinization of pores, controls/inhibits skin sebum to inhibit imperforation of pores, and helps pore tightening, thereby realizing an effect of controlling pores.

The term "skin pigmentation" means sub-epithelial deposition of melanin pigment broken by skin irritation, such as wounds, inflammation or continuous friction. Particularly, there is a tendency for melanin pigment to be deposited increasingly while skin inflammatory diseases, such as acne or dermatitis, occur and then disappear.

The composition according to an embodiment prevents, improves or treats skin pigmentation. Particularly, the composition prevents, improves and treats acne causing skin pigmentation, and inhibits or prevents production of melanin, skin pigment, thereby preventing, improving or treating skin pigmentation occurring after inflammatory diseases, such as acne.

The composition including hexamidine or a derivative or pharmaceutically acceptable salt thereof in combination with retinoid or a derivative or pharmaceutically acceptable salt thereof has higher effects of reducing the number of acne lesions and the number and area of sebaceous sites, controlling pores, and preventing, improving or treating skin pigmentation, as compared to a composition containing hexamidine or a derivative or pharmaceutically acceptable salt thereof alone, or containing retinoid or a derivative or pharmaceutically acceptable salt thereof alone.

The composition including hexamidine or a derivative or pharmaceutically acceptable salt thereof in combination with retinoid or a derivative or pharmaceutically acceptable salt thereof, as active ingredients, may further comprise a ceramide. Ceramides include not only natural ceramides that are intercellular lipids but also pseudo-ceramides having a chemical structure and effectiveness similar to natural ceramides. Ceramides are one of the intercellular lipids and are known to have functions as skin protection barriers, and moisture-retaining and corneous layer-protecting functions.

Particular examples of natural ceramides include at least one selected from the group consisting of ceramide 1, ceramide 2, ceramide 3, ceramide 4, ceramide 5, ceramide 6, ceramide 7, and ceramide 8.

Pseudo-ceramides are synthetic materials having skin-protecting activities and moisture-retaining activities similar to those activities of natural ceramides. Particular examples of pseudo-ceramides may include at least one selected from the group consisting of the following Chemical Formulae 1 to 6, but are not limited thereto.

[Chemical Formula 1]

wherein R is a $C_9$-$C_{21}$ saturated or unsaturated aliphatic chain.

[Chemical Formula 2]

wherein n is 1 or 2; and each of R and R' represents a $C_9$-$C_{21}$ saturated or unsaturated aliphatic chain.

[Chemical Formula 3]

wherein m and n are the same or different, and each represents an integer of 1-3; k and l are the same or different, and each represents 1 or 2; j is 0 or 1; R and R' are the same or different, and each represents a $C_1$-$C_{31}$ linear or branched, saturated or unsaturated alkyl group containing a hydroxyl group or not; $A^1$, $A^2$ and $A^3$ are the same or different, and each represents H or any one of the substituents having the following structures, with the proviso that $A^1$, $A^2$ and $A^3$ are not H at the same time:

wherein each of M, $M^1$ and $M^2$ is selected from the group consisting of alkali metals, lysine, arginine, hystidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal.

[Chemical Formula 4]

wherein R and R' are the same or different, and each represents a $C_{10}$-$C_{32}$ linear or branched, saturated or unsaturated alkyl group containing a hydroxyl group or not; $R^3$ and $R^4$ are the same or different, and each represents H or a $C_1$-$C_4$ alkyl or hydroxyalkyl group;
$R^5$ is —$CH_2CH_2OA$ or any one of the substituents having the following structures:

wherein each of M, $M^1$ and $M^2$ is selected from the group consisting of alkali metals, lysine, arginine, hystidine, triethanolamine, ammonia, polyquaternium-4, polyquaternium-6, polyquaternium-7, polyquaternium-10, polyquaternium-11, polyquaternium-16, lauryldimethylbenzylammonium chloride and stearyldimethylbenzylammonium chloride, and L is an alkaline earth metal.

[Chemical Formula 5]

wherein m and n are the same or different, and each represents an integer of 1-4; R and R' are the same or different, and each represents a $C_1$-$C_{31}$ linear or branched, saturated or unsaturated alkyl group containing a hydroxyl group or not; and $A_1$ and $A_2$ are the same or different, and each represents H or any one of the substituents having the following structures:

wherein each of M, M¹ and M² is an alkali metal or nitrogen-containing organic base, and L is an alkaline earth metal.

[Chemical Formula 6]

wherein m and n are the same or different, and each represents an integer of 1-3;
k and l are the same or different, and each represents 1 or 2;
j is 0 or 1;
$A^1$, $A^2$ and $A^3$ are the same or different, and each represents H or any one of the substituents having the following structures:

wherein each of M, M¹ and M² is an alkali metal or nitrogen-containing organic base, and L is an alkaline earth metal; and
R is a substituent represented by the following formula:

wherein B is a methyl group at 5-, 7- or 8-position of tocopherol; m is an integer of 1-3; and D is —$CH_2(CH_3)$—CH— or —$CH(CH_3)$=C—.

The compounds represented by the above Chemical Formulae 1-6 are excellent in skin moisturization and skin barrier function recovery, and are commercially available as PC104, PC102, PC107 or the like.

While the compositions containing such retinoids are effective for preventing hyperkeratinization of pores and for controlling skin sebum, they may cause irritation on the epidermal layer at a site other than pore through a transdermal delivery path. Therefore, when a relatively high concentration of retinoids is used, side effects including skin blush, itch or stinging may occur. However, when ceramides are further incorporated into a composition containing retinoids, it is possible to alleviate skin irritation caused by retinoids. Ceramides are intercellular lipids of callus present at the outermost portion of the epidermis except pores, and serve to enhance a barrier effect of the skin corny layer. Therefore, it is thought that when using ceramides in combination with retinoids, a layer formed from ceramides reduces direct contact between retinoids and the skin. Even when irritation occurs due to retinoids, ceramides reinforce a skin barrier layer to facilitate rapid recovery of skin, leading to alleviation of skin irritation caused by retinoids. Further, addition of ceramides allows the composition to retain skin moisture and to protect the corny layer, thereby enhancing effects of skin moisturization and skin improvement.

According to an embodiment, hexamidine or a derivative or pharmaceutically acceptable salt thereof may be used in the composition in an amount of 0.0001 wt % to 15 wt % based on the total weight of the composition. When the amount is less than 0.0001 wt %, it is not possible to obtain a desired effect. When the amount is more than 15 wt %, skin irritation may occur and the stability of a dosage form may be degraded.

According to an embodiment, retinoid or a derivative or pharmaceutically acceptable salt thereof may be used in the composition in an amount of 0.0001 wt % to 15 wt % based on the total weight of the composition. When the amount is less than 0.0001 wt %, it is not possible to obtain a desired effect. When the amount is more than 15 wt %, skin irritation may occur.

According to an embodiment, a ceramide may be used in the composition in an amount of 0.001 wt % to 10 wt % based on the total weight of the composition. When the amount is less than 0.001 wt %, it is not possible to obtain a desired effect. When the amount is more than 10 wt %, the stability of a dosage form may be degraded.

In another aspect, there is provided a cosmetic composition including the composition hexamidine or a derivative or pharmaceutically acceptable salt thereof in combination with retinoid or a derivative or pharmaceutically acceptable salt thereof, as active ingredients. The cosmetic composition may be provided as a cosmetic product having a formulation using a cosmetically or dermatologically acceptable medium or base. Such formulations include any forms suitable for topical application, and particular examples thereof include solution, gel, solid, anhydrous slurry products, oil in water emulsion, water in oil emulsion, multiemulsion, suspension, microemulsion, microcapsules, microgranules or ionic (liposome) and non-ionic follicular dispersion, or cream, skin, lotion, powder, ointment, spray, cleanser or conceal stick. The composition disclosed herein may be used in the form of foam or an aerosol composition further including a pressurized propellant. Such compositions may be obtained by a conventional method.

The cosmetic composition may further include other adjuvants currently used in the field of cosmetics or dermatology, and particular examples thereof include fatty materials, organic solvents, solubilizing agents, concentrating agents, gelling agents, softening agents, antioxidants, suspending agents, stabilizers, foaming agents, fragrances, surfactants, water, ionic or non-ionic emulsifiers, fillers, metal ion blockers, chelating agents, preservatives, vitamins, protecting agents, wetting agents, essential oil, dyes, pigments, hydrophilic or oleophilic active agents, lipid follicles or other ingredients conventionally used in cosmetic products. Such adjuvants may be used in an amount generally known to those skilled in the art.

There is no particular limitation in formulation of the cosmetic composition and any formulation may be selected as desired. For example, the cosmetic composition may be provided as one or more formulations selected from the group consisting of skin softeners (skin lotion and milk lotion), nourishing lotion, essence, nourishing cream, massage cream, pack, gel, eye cream, eye essence, cleansing cream, cleansing foam, cleansing water, powder, cleanser, body lotion, body cream, body oil and body essence, but is not limited thereto.

In still another aspect, there is provided a pharmaceutical composition including hexamidine or a derivative or pharmaceutically acceptable salt thereof in combination with retinoid or a derivative or pharmaceutically acceptable salt thereof, as active ingredients.

When applying the composition disclosed herein to pharmaceuticals, a conventional inorganic or organic carrier is added to the composition as an active part, so that the composition may be formulated into a solid, semi-solid or liquid form for oral or parenteral administration. The active ingredients disclosed herein may be formulated with ease by a currently used method. In addition, surfactants, vehicles, colorants, spices, stabilizers, preservatives, antibacterial agents, hydrating agent, emulsification accelerators, suspending agents, salts and/or buffers for controlling osmotic pressure, and other conventional adjuvants may be used in a suitable manner.

For oral administration, tablets, pills, granules, soft and hard capsules, dusts, fine particles, powder, liquid, emulsion, syrup, pellets or the like may be used. Such formulations may further include diluents (e.g. lactose, dextrose, sucrose, mannitol, sorbitol, cellulose and glycine) or lubricants (e.g. silica, talc, stearic acid and magnesium or calcium salts thereof and polyethylene glycol), in addition to the active ingredients. Tablets may include a binder such as magnesium aluminum silicate, starch paste, gelatin, tragacanth, methyl cellulose, sodium carboxymethyl cellulose or polyvinyl pyrrolidine. If necessary, tablets may further include other pharmaceutical additives, for example, a disintegrating agent, such as starch, agar, alginic acid or a sodium salt thereof, adsorbing agent, coloring agent, flavor or sweetener. Such tablets may be obtained by conventional mixing, granulation or coating processes.

Meanwhile, formulations for parenteral administration include skin application formulations, or injection formulation, drops, lotion, ointment, gel, cream, suspension, emulsion, suppositories, patches or spray formulations, but are not limited thereto.

The pharmaceutical composition disclosed herein may be administered via oral, parenteral, rectal, local, transdermal, intravenous, intramuscular, intraperitoneal, subcutaneous routes, or the like.

In addition, the dose of active ingredients may be varied with the age, sex and body weight of a subject to be treated, particular disease or pathological condition to be treated, severity of disease or pathological condition, administration route and the judgment of a prescriber. Determination of the effective dose may be made by those skilled in the art based on the above-mentioned factors. In general, the effective doe may be between 0.001 mg/kg/day and 2,000 mg/kg/day, particularly between 0.5 mg/kg/day and 2.5 mg/kg/day.

MODE FOR INVENTION

The examples and experiments will now be described. The following examples and experiments are for illustrative purposes only and not intended to limit the scope of this disclosure.

Example 1 and Comparative Examples 1 and 2

Comparative Examples 1 and 2 and Example 1 are prepared according to the compositions as shown in the following Table 1. First, glycerin, sodium hydroxide and hexamidine (and/or retinol) are dissolved into purified water. In a separate container, hydrogenated castor oil is dissolved into alcohol. Then, the two parts are agitated together at a high speed, and Carbomer is added thereto to increase the viscosity. In this manner, solubilized gels are obtained as Comparative Examples 1 and 2 and Example 1.

TABLE 1

|  | Comparative Example 1 | Comparative Example 2 | Example 1 |
| --- | --- | --- | --- |
| Purified water | 83.90% | 83.95% | 83.85% |
| Hexamidine | 0.10% | — | 0.10% |
| Retinol | — | 0.05% | 0.05% |
| Glycerin | 10% | 10% | 10% |
| Carbomer | 0.50% | 0.50% | 0.50% |
| Alcohol | 3% | 3% | 3% |
| Hydrogenated castor oil | 2% | 2% | 2% |
| Sodium hydroxide | 0.50% | 0.50% | 0.50% |

Test Example 1

Evaluation of Effect of Preventing, Improving or Treating Acne

Each of the solubilized gels according to Comparative Examples 1 and 2 and Example 1 is applied to subjects including twenty healthy male and female adults, or nothing is applied (no treatment) to the subjects. Facial Stage System is used to obtain optical photographs and UV photographs, before the application and 2 weeks and 4 weeks after the application. The photographs are taken after the subjects clean their faces and wait for 15 minutes under a constant-temperature/constant-humidity condition to stabilize their skin conditions.

After taking the optical photographs, acne sites exposed on the skin surfaces are evaluated by the naked eyes and any changes in the acne sites are monitored. After taking the UV photographs, skin acne sites are observed by the naked eyes and the number of acne lesions is determined. Based on the determined value, a rate of change (%) in the number of acne lesions after the application is shown in FIG. 1 based on the number before the application.

Figure 1:
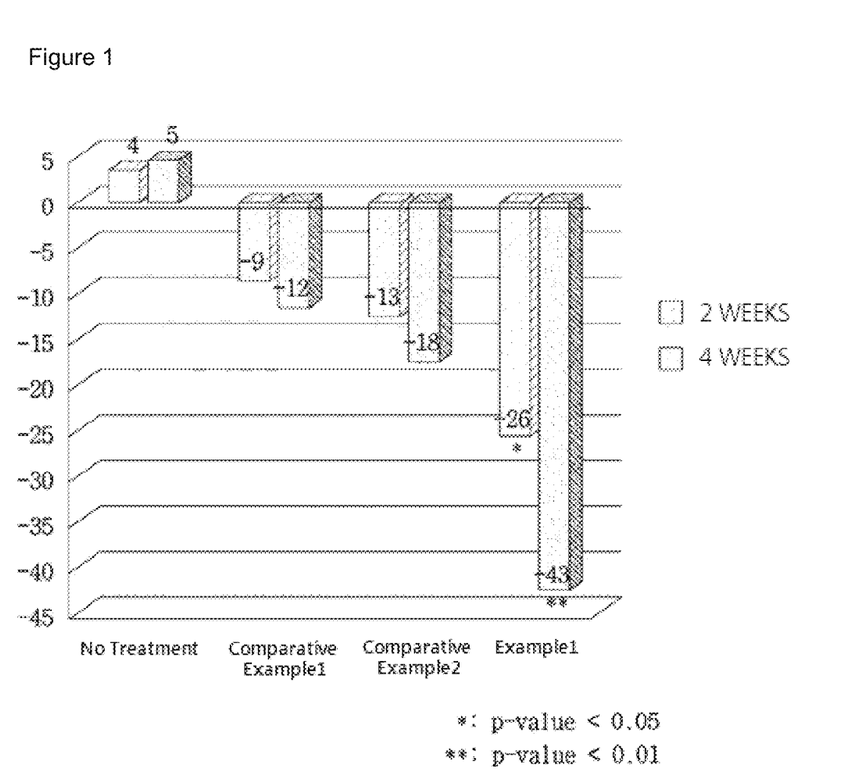
FIG. 1 is a graph showing the results of Test Example 1 in which a rate of change (%) in number of acne lesions after the application of hexamidine, retinol, or hexamidine and retinol on the face is compared with the number of acne lesions in the case of no treatment.

As can be seen from FIG. 1, Example 1 containing both hexamidine and retinol provides the highest decrease in the number of acne lesions, which is about 2-3 times of the results of Comparative Examples 1 and 2. Therefore, it is shown that the composition containing both hexamidine and retinol is more effective for preventing, improving or treating acne as compared to the composition containing either hexamidine or retinol, or to the case of nothing applied.

Test Example 2

Evaluation of Effect of Reducing Sebum

Each of the solubilized gels according to Comparative Examples 1 and 2 and Example 1 is applied to subjects including twenty healthy male and female adults, or nothing is applied to the subjects. Skin Touch System is used to obtain UV photographs, before the application and 2 weeks and 4 weeks after the application. The photographs are taken after the subjects clean their faces and wait for 15 minutes under a constant-temperature/constant-humidity condition to stabilize their skin conditions.

Figure 2:
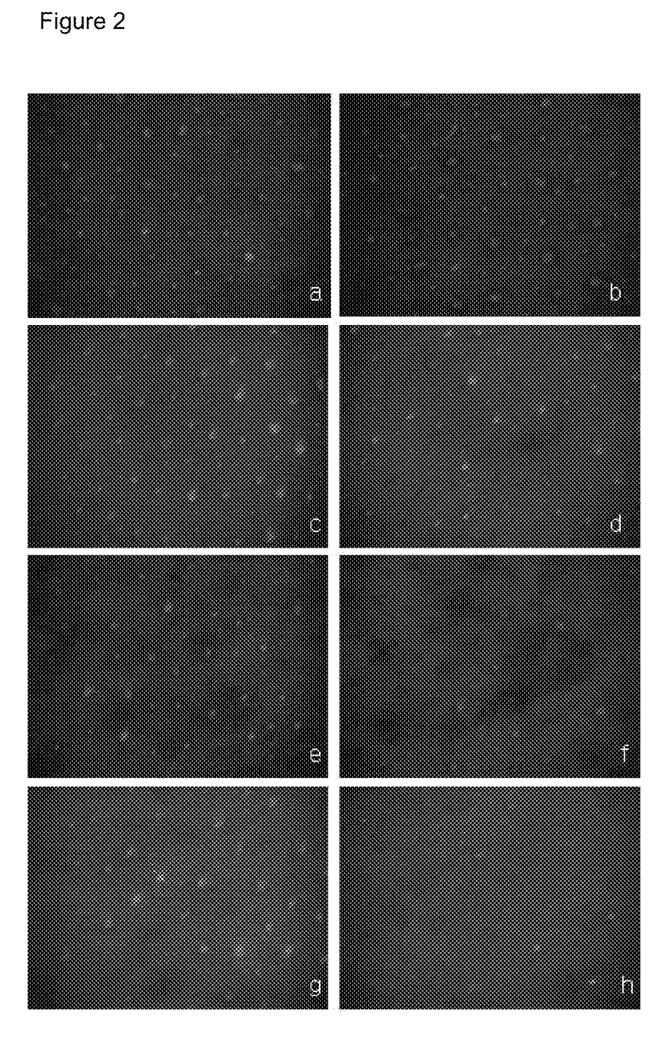

Exaggerated images of sebaceous sites are obtained from the UV photographs and are shown in FIG. 2. In FIG. 2, Portions a and b are the photographs before the test and 4 weeks after the test using no treatment; Portions c and d are the photographs before the test and 4 weeks after the test using application of Comparative Example 1; Portions e and f are the photographs before the test and 4 weeks after the test using application of Comparative Example 2; and Portions g and h are the photographs before the test and 4 weeks after the test using application of Example 1. In FIG. 2, sebum is shown in the form of light dots (red dots represent oxidized sebum, while green and yellow dots represent non-oxidized sebum). As can be seen from Portions a and b showing the results before the test and 4 weeks after the test using no treatment, there is little change in the number and area of sebaceous sites. When comparing Portions c and e showing the results before the tests using application of Comparative Examples 1 and 2, respectively, with Portions d and f showing the results 4 weeks after the tests using application of Comparative Examples 1 and 2, respectively, Comparative Examples 1 and 2 provide a slight decrease in the number and area of sebaceous sites. However, Comparative Examples 1 and 2 show a smaller decrease as compared to Portions g and h showing the results using application of Example 1. In brief, it can be seen that application of Example 1 containing both hexamidine and retinol provides the largest decrease in the number and area of sebaceous sites.

Figure 3:
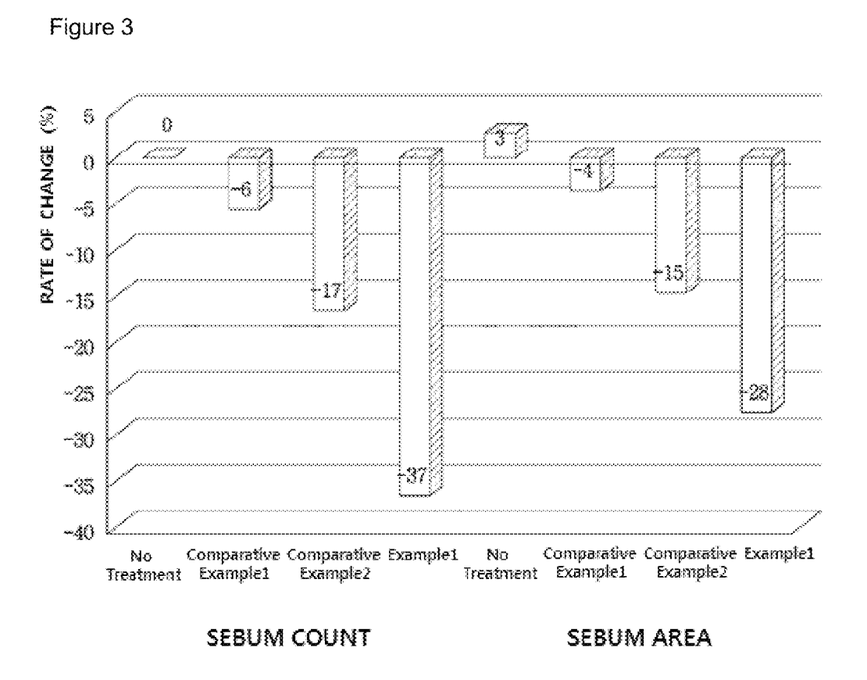
FIG. 3 is a graph showing the results of Test Example 2 in which a rate of change (%) in sebaceous sites after the application of hexamidine, retinol, or hexamidine and retinol on the face is compared with the sebaceous sites in the case of no treatment.

In addition, based on the above results, the number and area of sebaceous sites are rated through a skin touch operating program and image pro-analysis program. From the rating results, the significance is determined as p value obtained through a paired T-test, and variances are analyzed. Based on the rating results, a rate of change (%) in sebaceous sites after the application is shown in FIG. 3. As can be seen from FIG. 3, Example 1 provides the largest decrease in the number and area of sebaceous sites, which is about 2-6 times of the results of Comparative Examples 1 and 2. Therefore, it is shown that the composition containing both hexamidine and retinol is more effective for reducing the number and area of sebaceous sites as compared to the composition containing either hexamidine or retinol, or to the case of nothing applied.

Test Example 3

Evaluation of Effect of Controlling Pores

Each of the solubilized gels according to Comparative Examples 1 and 2 and Example 1 is applied to subjects including twenty healthy male and female adults, or nothing is applied to the subjects. Skin Touch System is used to obtain optical photographs, before the application and 2 weeks and 4 weeks after the application. The photographs are taken after the subjects clean their faces and wait for 15 minutes under a constant-temperature/constant-humidity condition to stabilize their skin conditions.

Figure 4:
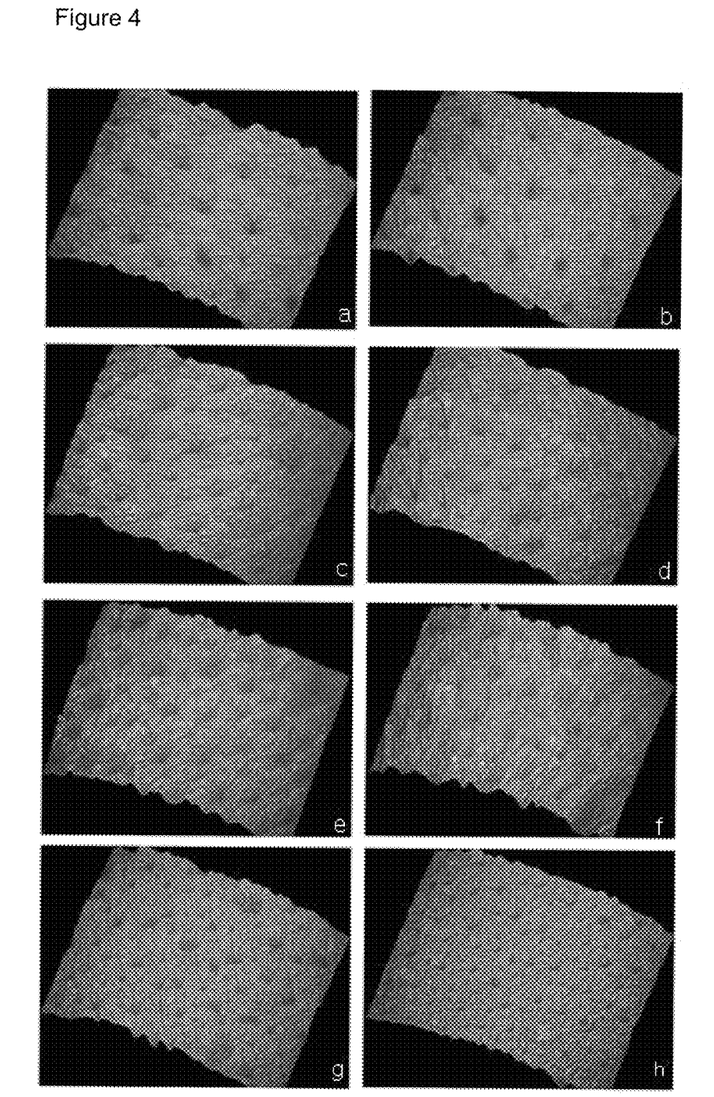
FIG. 4 shows optical photographs showing the results of Test Example 3 in which pore sites are investigated before the test and 4 weeks after the test using no treatment, and using application of hexamidine, retinol, or hexamidine and retinol on the face (Portions a and b are the photographs before the test and 4 weeks after the test using no treatment; Portions c and d are the photographs before the test and 4 weeks after the test using application of Comparative Example 1; Portions e and f are the photographs before the test and 4 weeks after the test using application of Comparative Example 2; and Portions g and h are the photographs before the test and 4 weeks after the test using application of Example 1)

Exaggerated three-dimensional images of pore sites are obtained from the optical photographs and are shown in FIG. 4. In FIG. 4, Portions a and b are the photographs before the test and 4 weeks after the test using no treatment; Portions c and d are the photographs before the test and 4 weeks after the test using application of Comparative Example 1; Portions e and f are the photographs before the test and 4 weeks after the test using application of Comparative Example 2; and Portions g and h are the photographs before the test and 4 weeks after the test using application of Example 1. When comparing Portion a showing the result before the test using no treatment and Portions c and e showing the results before the tests using application of Comparative Examples 1 and 2, respectively, with Portions b, d and f showing the results 4 weeks after the tests, there is little change in pore sizes. On the contrary, when comparing Portion g showing the result before the test using application of Example 1 with Portion h showing the results 4 weeks after the test using application of Example 1, there is a significant decrease in pore sizes. In other words, it can be seen that application of Example 1 containing both hexamidine and retinol provides the highest effect of reducing pore sizes.

Therefore, it is shown that the composition containing both hexamidine and retinol is more effective for reducing the size of pokes, and thus has a higher pore-controlling effect, as compared to the composition containing either hexamidine or retinol, or to the case of nothing applied.

Test Example 4

Evaluation of Effect of Preventing, Improving or Treating Skin Pigmentation

To a 48-well plate, Melan-a melanocytes ($2.0 \times 10^4$) are introduced and cultured at a temperature of 37° C. under 10% $CO_2$ atmosphere. In a Roswell Park Memorial Institute (RPMI) medium containing 10% fetal bovine serum (FBS), the culture is treated for 5 days with 10 µM of arachidonic acid, 5 µM of linoleic acid and 10 nM of DHT as stimulants. Then, in a RPMI medium containing 10% FBS, treatment is carried out for 5 days with hydroquinone and albutin 200 ppm as a positive control, with Example 1 and Comparative Examples 1 and 2 as test groups, and with the stimulants only as a negative control. In addition, a control test is also carried out with no treatment. Then, melanin is dissolved in 1N NaOH and optical density (O.D.) is measured at 405 nm to count melanin by the Lowry method. According to the following Mathematical Formula 1, the melanin content of each group is calculated based on that of the negative control. The results are shown in FIG. 5.

Melanin Content (%)=(Absorbance of Each Test Group/Absorbance of Negative Control)×100     [Mathematical Formula 1]

Figure 5:
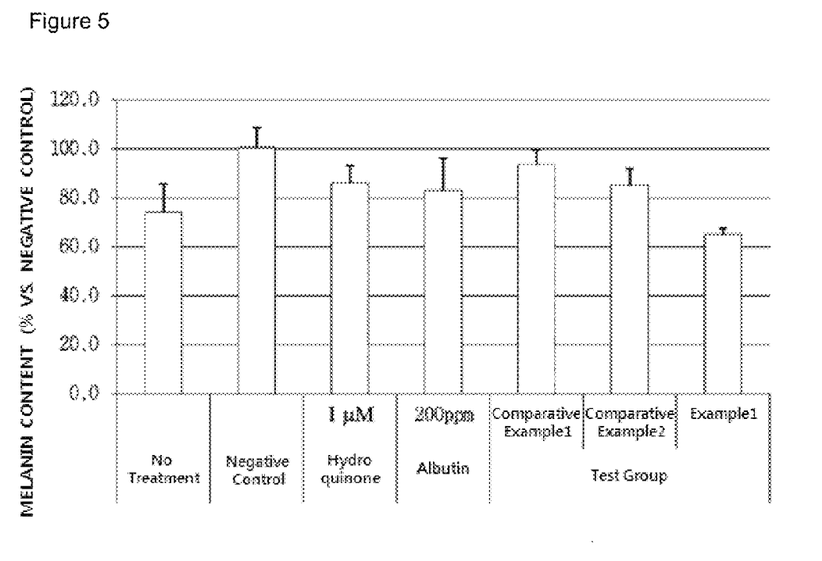
FIG. 5 is a graph showing the results of Test Example 4 in which an effect of inhibiting melanin formation of a composition containing hexamidine in combination with retinol is compared with the same effect of the positive control, negative control and the compositions of Comparative Examples.

As can be seen from FIG. 5, the composition containing both hexamidine and retinol shows a lower melanin content as compared to the composition containing either hexamidine or retinol, and thus provides a higher effect of inhibiting melanin formation. In addition, the composition containing both hexamidine and retinol is more effective than the positive control, hydroquinone 1 µM and albutin 200 ppm. Therefore, it is shown that the composition containing both hexamidine and retinol is highly effective for preventing, improving or treating skin pigmentation caused by deposition of melanin on skin.

Examples 2, 3 and 4 and Comparative Example 3

Examples 2, 3 and 4 and Comparative Example 3 are prepared according to the compositions as shown in the following Table 2. First, glycerin, sodium hydroxide, hexamidine and retinol are dissolved into purified water. In a separate container, hydrogenated castor oil and ceramides are dissolved into alcohol. Then, the two parts are agitated together at a high speed, and Carbomer is added thereto to increase the viscosity. In this manner, solubilized gels are obtained as Examples 2, 3 and 4 and Comparative Example 3.

TABLE 2

|  | Comparative Example 3 | Example 2 | Example 3 | Example 4 |
|---|---|---|---|---|
| Purified water | 83.6% | 83.40% | 82.60% | 78.60% |
| Ceramides | — | 0.20% | 1.0% | 5.0% |
| Hexamidine | 0.1% | 0.1% | 0.1% | 0.1% |
| Retinol | 0.3% | 0.3% | 0.3% | 0.3% |
| Glycerin | 10% | 10% | 10% | 10% |
| Carbomer | 0.5% | 0.5% | 0.5% | 0.5% |
| Alcohol | 3% | 3% | 3% | 3% |
| Hydrogenated castor oil | 2% | 2% | 2% | 2% |
| Sodium hydroxide | 0.50% | 0.50% | 0.50% | 0.50% |

Test Example 5

Evaluation of Effect of Alleviating Skin Irritation Through Addition of Pseudo-Ceramides Examples 2, 3 and 4 and Comparative Example 3 containing hexamidine and retinol 10,000 IU and having different contents of pseudo-ceramides are applied to the lower portion of the left arm of each subject of twenty healthy adults (10 men and 10 women) in an amount of 2 μL/cm² for 1 week. The test portion is exposed to the sunlight and a degree of skin irritation is determined as an erythema index. Before determining the degree of skin irritation in Comparative Example 3 and Examples 2, 3 and 4, the subjects clean their lower arm portions and wait for 15 minutes under a constant-temperature/constant-humidity condition to stabilize their skin conditions. The results are shown in the graph of FIG. 6.

Figure 6:
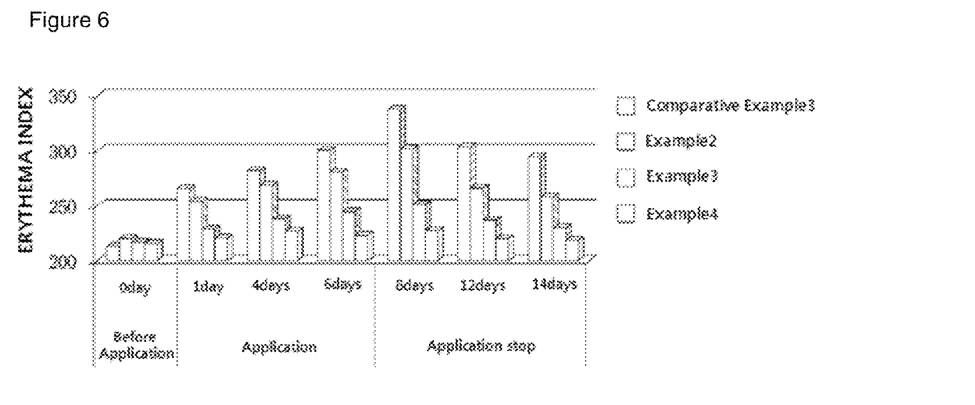
FIG. 6 is a graph showing the results of Test Example 5, in which a degree of skin irritation is determined as an erythema index after the application of a composition containing hexamidine in combination with retinol, and after the application of a composition containing each of hexamidine, retinol and 0.2%, 1% and 5% of pseudo-ceramides.

In FIG. 6, a higher number indicates less erythema. When evaluating the overall results, exposure to the sunlight after the application of hexamidine and retinol tends to increase an erythema index, and the erythema index tends to decrease when the application is stopped. Examples 2, 3 and 4 including pseudo-ceramides provides a significant decrease in erythema index as compared to Comparative Example 3 including no pseudo-ceramides. Particularly, Example 4 including 5% pseudo-ceramides causes little erythema even when the test portion is exposed to the sunlight after the application of hexamidine and retinol. Therefore, it is shown that use of pseudo-ceramides in combination with hexamidine and retinol alleviates skin irritation and the effect of alleviating skin irritation is in proportion to the content of pseudo-ceramides.

The formulation examples will now be described in detail for the pharmaceutical composition and cosmetic composition using the composition including hexamidine or a derivative or pharmaceutically acceptable salt thereof in combination with retinoid or a derivative or pharmaceutically acceptable salt thereof, as active ingredients. However, the pharmaceutical composition and the cosmetic composition disclosed herein may be formulated in various forms other than those described hereinafter. The following formulation examples are for illustrative purposes only and not intended to limit the scope of this disclosure.

Formulation Example 1

Ointment for Skin Application

Ointment is obtained in a conventional manner according to the composition as shown in the following Table 3.

TABLE 3

| Ingredient | Amount (wt %) |
|---|---|
| Purified water | Balance |
| Glycerin | 8.0 |
| Butylene glycol | 4.0 |
| Liquid paraffin | 15.0 |
| Betaglucan | 7.0 |
| Carbomer | 0.1 |
| Hexamidine and retinoid | 1.0 |
| Caprylic/Capric triglycerides | 3.0 |
| Squalane | 1.0 |
| Cetearyl glucoside | 1.5 |
| Sorbitan stearate | 0.4 |
| Cetearyl alcohol | 1.0 |
| Preservative | q.s. |
| Fragrance | q.s. |
| Pigment | q.s. |
| Beeswax | 4.0 |

Formulation Example 2

Skin Softener (Skin Lotion)

Skin softener is obtained in a conventional manner according to the composition as shown in the following Table 4.

TABLE 4

| Ingredient | Amount (wt %) |
|---|---|
| Hexamidine and retinoid | 0.1 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Preservative, pigment and fragrance | q.s. |
| Purified water | Balance |

Formulation Example 3

Nourishing Cream

Nourishing cream is obtained in a conventional manner according to the composition as shown in the following Table 5.

TABLE 5

| Ingredient | Amount (wt %) |
|---|---|
| Purified water | Balance |
| Glycerin | 3.0 |
| Butylene glycol | 3.0 |

TABLE 5-continued

| Ingredient | Amount (wt %) |
| --- | --- |
| Liquid paraffin | 7.0 |
| Betaglucan | 7.0 |
| Carbomer | 0.1 |
| Hexamidine and retinoid | 3.0 |
| Caprylic/capric triglycerides | 3.0 |
| Squalane | 5.0 |
| Cetearyl glycoside | 1.5 |
| Sorbitan stearate | 0.4 |
| Polysorbate 60 | 1.2 |
| Preservative | q.s. |
| Fragrance | q.s. |
| Pigment | q.s. |
| Triethanolamine | 0.1 |

Formulation Example 4

Massage Cream

Massage cream is obtained in a conventional manner according to the composition as shown in the following Table 6.

TABLE 6

| Ingredient | Amount (wt %) |
| --- | --- |
| Purified water | Balance |
| Glycerin | 8.0 |
| Butylene glycol | 4.0 |
| Liquid paraffin | 45.0 |
| Betaglucan | 7.0 |
| Carbomer | 0.1 |
| Hexamidine and retinoid | 1.0 |
| Caprylic/capric triglycerides | 3.0 |
| Beeswax | 4.0 |
| Cetearyl glucoside | 1.5 |
| Sorbitan cesquioleate | 0.9 |
| Vaseline | 3.0 |
| Preservative | q.s. |
| Fragrance | q.s. |
| Pigment | q.s. |
| Paraffin | 1.5 |

Formulation Example 5

Pack

Pack is obtained in a conventional manner according to the composition as shown in the following Table 7.

TABLE 7

| Ingredient | Amount (wt %) |
| --- | --- |
| Purified water | Balance |
| Glycerin | 4.0 |
| Polyvinyl alcohol | 15.0 |
| Hyaluronic acid extract | 5.0 |
| Betaglucan | 7.0 |
| Allantoin | 0.1 |
| Hexamidine and retinoid | 0.5 |

TABLE 7-continued

| Ingredient | Amount (wt %) |
| --- | --- |
| Nonyl phenyl ether | 0.4 |
| Polysorbate 60 | 1.2 |
| Preservative | q.s. |
| Fragrance | q.s. |
| Pigment | q.s. |
| Ethanol | 6.0 |

We claim:

1. A method for improving skin condition of a subject, comprising:
administering to the subject a composition comprising an effective amount of hexamidine, retinol, and ceramide that improve skin condition in the subject;
wherein the ceramide is in an amount of 0.2 wt % to 5.0 wt % based on a total weight of the composition;
wherein the hexamidine is in an amount of 0.1 wt % based on the total weight of the composition,
wherein the retinol is in an amount of 0.05 wt % to 0.3 wt % based on the total weight of the composition,
wherein the improving skin condition of the subject is selected from the group consisting of improving or treating acne of the subject, controlling sebum of the subject, controlling pores of the subject, and improving or treating skin pigmentation of the subject,
wherein the ceramide alleviates skin irritation caused by the retinol, and
wherein the ceramide is represented by Chemical Formula 2:

Chemical Formula 2 wherein n is 1 or 2; and each of R and R' represents a $C_9$-$C_{21}$ saturated or unsaturated aliphatic chain.

2. The method according to claim 1, wherein the improving skin condition of the subject comprises improving or treating acne of the subject.

3. The method according to claim 1, wherein the improving skin condition of the subject comprises controlling sebum of the subject.

4. The method according to claim 1, wherein the improving skin condition of the subject comprises controlling pores of the subject.

5. The method according to claim 1, wherein the improving skin condition of the subject comprises improving or treating skin pigmentation of the subject.

* * * * *